United States Patent
Hunt et al.

(10) Patent No.: US 6,506,208 B2
(45) Date of Patent: Jan. 14, 2003

(54) SURGICAL INSTRUMENT

(76) Inventors: Robert B. Hunt, 129 Dedham St., Dover, MA (US) 02030; Gerald S. Melsky, 2 Dewey Rd., Lexington, MA (US) 02420; Stephen C. Evans, 22 Carlisle Rd, Westford, MA (US) 01886; Gary Whipple, 406 Newport Ave., South Attleboro, MA (US) 02703; Richard Wisdom, 3 Holmfield Ave., Mattapan, MA (US) 02126

(*) Notice: Subject to any disclaimer, the term of this patent is extended or adjusted under 35 U.S.C. 154(b) by 0 days.

(21) Appl. No.: 09/973,304

(22) Filed: Oct. 9, 2001

(65) Prior Publication Data

US 2002/0072766 A1 Jun. 13, 2002

Related U.S. Application Data

(63) Continuation-in-part of application No. 09/519,103, filed on Mar. 6, 2000, now Pat. No. 6,358,268.

(51) Int. Cl.$^7$ .............................................. A61B 17/28
(52) U.S. Cl. ....................................... 606/205; 606/208
(58) Field of Search ........................... 606/205–211, 51, 606/52, 170, 174; 128/751

(56) References Cited

U.S. PATENT DOCUMENTS

| | | | |
|---|---|---|---|
| 3,894,336 A | 7/1975 | Desimone |
| 4,164,225 A | 8/1979 | Johnson et al. |
| 5,071,419 A | 12/1991 | Rydell et al. |
| 5,163,942 A | 11/1992 | Rydell |
| 5,171,258 A | 12/1992 | Bales et al. |
| 5,171,311 A | 12/1992 | Rydell et al. |
| 5,192,280 A | 3/1993 | Parins |
| 5,197,963 A | 3/1993 | Parins |
| 5,207,213 A | 5/1993 | Auhill et al. |
| 5,217,458 A | 6/1993 | Parins |
| 5,250,047 A | 10/1993 | Rydell |
| 5,258,006 A | 11/1993 | Rydell et al. |
| 5,269,754 A | 12/1993 | Rydell |
| 5,304,147 A | 4/1994 | Johnson et al. |
| 5,312,434 A | 5/1994 | Crainich |
| 5,320,636 A | 6/1994 | Slater |
| 5,330,471 A | 7/1994 | Eggers |
| 5,334,198 A | 8/1994 | Hart et al. |
| 5,342,359 A | 8/1994 | Rydell |
| 5,342,381 A | 8/1994 | Tidemand |
| 5,352,222 A | 10/1994 | Rydell |
| 5,356,408 A | 10/1994 | Rydell |
| 5,360,428 A | 11/1994 | Hutchinson, Jr. |
| 5,383,888 A | 1/1995 | Zvenyatsky et al. |
| 5,391,166 A | 2/1995 | Eggers |

(List continued on next page.)

FOREIGN PATENT DOCUMENTS

| | | |
|---|---|---|
| WO | WO 89/02719 | 4/1989 |
| WO | WO 96/02182 | 2/1996 |
| WO | WO 97/18746 | 5/1997 |
| WO | WO 99/05958 | 2/1999 |
| WO | WO 00/06033 | 2/2000 |

Primary Examiner—Kevin T. Truong
(74) Attorney, Agent, or Firm—Iandiorio & Teska

(57) ABSTRACT

A multi-function laparoscopic instrument with an end effector assembly including at least first and second movable members, a first actuator coupled to the first movable member, a second actuator coupled to the second movable member, and a handle assembly. The handle assembly includes a drive mechanism, at least one movable trigger pivotably connected with the drive mechanism, and a switching mechanism coupled to the drive mechanism and having at least two positions, a first position in which the drive mechanism is engaged with the first actuator to operate the first movable member when the movable trigger is activated and, a second position in which the drive mechanism is engaged with the second actuator to operate the second movable member when the movable trigger is activated.

55 Claims, 13 Drawing Sheets

U.S. PATENT DOCUMENTS

| | | | |
|---|---|---|---|
| 5,403,312 A | | 4/1995 | Yates et al. |
| 5,403,332 A | | 4/1995 | Christoudias |
| 5,445,638 A | | 8/1995 | Rydell et al. |
| 5,456,684 A | | 10/1995 | Schmidt et al. |
| 5,462,546 A | | 10/1995 | Rydell |
| 5,478,347 A | | 12/1995 | Aranyi |
| 5,480,409 A | | 1/1996 | Riza |
| 5,496,317 A | | 3/1996 | Goble et al. |
| 5,514,134 A | | 5/1996 | Rydell et al. |
| 5,522,830 A | | 6/1996 | Aranyi |
| 5,527,313 A | | 6/1996 | Scott et al. |
| 5,531,744 A | | 7/1996 | Nardella et al. |
| 5,540,685 A | | 7/1996 | Parins et al. |
| 5,569,164 A | | 10/1996 | Lurz |
| 5,569,243 A | | 10/1996 | Kortenbach et al. |
| 5,569,843 A | | 10/1996 | Kortenbach et al. |
| 5,571,100 A | | 11/1996 | Goble et al. |
| 5,573,535 A | | 11/1996 | Viklund |
| 5,578,052 A | | 11/1996 | Koros et al. |
| 5,599,350 A | | 2/1997 | Schulze et al. |
| 5,603,711 A | | 2/1997 | Parins et al. |
| 5,603,723 A | | 2/1997 | Aranyi et al. |
| 5,626,608 A | * | 5/1997 | Cuny et al. .................. 606/205 |
| 5,637,110 A | | 6/1997 | Pennybacker et al. |
| 5,647,840 A | | 7/1997 | D'Amelio et al. |
| 5,658,281 A | | 8/1997 | Heard |
| 5,665,100 A | | 9/1997 | Yoon |
| 5,674,220 A | | 10/1997 | Fox et al. |
| 5,735,849 A | | 4/1998 | Baden et al. |
| 5,741,285 A | | 4/1998 | McBrayer et al. |
| 5,743,906 A | | 4/1998 | Parins et al. |
| 5,752,951 A | | 5/1998 | Yanik |
| 5,766,166 A | | 6/1998 | Hooven |
| 5,779,701 A | | 7/1998 | McBrayer et al. |
| 5,797,927 A | | 8/1998 | Yoon |
| 5,797,941 A | | 8/1998 | Schulze et al. |
| 5,827,281 A | | 10/1998 | Levin |
| 5,827,323 A | * | 10/1998 | Klieman et al. ............ 606/205 |
| 5,833,690 A | | 11/1998 | Yates et al. |
| 5,851,214 A | | 12/1998 | Larsen et al. |
| 5,893,875 A | | 4/1999 | O'Connor et al. |
| 5,895,370 A | | 4/1999 | Edwards et al. |
| 5,906,629 A | | 5/1999 | Oren et al. |
| 5,908,420 A | | 6/1999 | Parins et al. |
| 6,022,334 A | | 2/2000 | Edwards et al. |
| 6,074,408 A | | 6/2000 | Freeman |
| RE36,795 E | | 7/2000 | Rydell |
| 6,117,158 A | * | 9/2000 | Measamer et al. .......... 606/208 |
| 6,190,386 B1 | | 2/2001 | Rydell |

* cited by examiner

SURGICAL INSTRUMENT

RELATED APPLICATIONS

This application is a continuation-in-part application of U.S. application Ser. No. 09/519,103 filed Mar. 6, 2000, now U.S. Pat. No. 6,358,268.

FIELD OF THE INVENTION

This invention relates to a surgical instrument and, in one example, a combined laparoscopic scissors and forceps device.

BACKGROUND OF THE INVENTION

Laparoscopic surgery is used to provide a wide variety of surgical procedures on a patient's abdomen. The application of laparoscopic methods continues to grow as techniques are refined and the associated surgical instruments are improved. Patients benefit from laparoscopic procedures because the methods employed minimize the amount of trauma associated with a given procedure. Hence, patient survival is enhanced and recovery times are decreased.

Prior art laparoscopic surgical instruments typically include a handle, a 33 centimeter length, 5 millimeter diameter shaft which can be inserted through a cannula placed in a patient's abdominal wall, and scissors or tissue grasping jaws (e.g., forceps) extending from the end of the shaft.

In some cases, laparoscopic graspers, and/or scissors and some other types of instruments have the ability to apply RF energy in order to locally vaporize tissue and thereby cut through it or to coagulate blood vessels. There are two common ways in which the RF energy is applied. In either method, current travels between two electrodes. In monopolar instruments, the surgical instrument serves as one electrode and the second electrode is a large surface area electrode placed on the patient. In bipolar instruments, both electrodes are disposed on the surgical instrument in close proximity to one another.

Many conventional laparoscopic surgical instruments tend to be clumsier than those used in conventional surgery. As explained above, in laparoscopic surgery, the surgical instruments are inserted through a cannula placed in the patient's abdominal wall. To keep patient trauma to a minimum, only a limited number of cannula are employed for a given procedure. Often, using existing surgical instruments, the instruments must be repeatedly removed from the cannula and replaced with different instruments and removed and replaced again. This process of repeated instrument exchanges greatly increases the time it takes to perform a given medical procedure.

Two commonly used laparoscopic instruments are scissors and tissue graspers. Scissors are used to dissect tissue, transect ligated vessels or other bodily ducts (such as fallopian tubes), trim sutures and ligatures and to perform other cutting functions. Graspers or forceps are used to coagulate and to grip and manipulate tissue and also to perform a variety of blunt dissecting procedures. Tissue is either grasped and pulled away from substrate tissue to which it is loosely connected or the blunt tips of the closed graspers are inserted between loosely connected tissue strata and then the tips are forced apart separating the tissue strata. The operation of ordinary scissors and forceps is very familiar to surgeons and non-medical personnel alike and their function and operation are somewhat intuitive. This fact remains true when scissors or forceps are incorporated into a traditional laparoscopic instrument.

Traditionally, when tissue cutting procedures are required, a scissors type laparoscopic instrument is used, and, when tissue grasping procedures are required, a forceps type laparoscopic instrument is used. Thus, the surgeon must either employ two cannulas or switch instruments depending on whether cutting or grasping procedures are required.

To overcome this problem, those skilled in the art have developed surgical instruments with detachable scissors and forceps end assemblies, and surgical instruments with combined scissors and forceps end assemblies.

For example, U.S. Pat. No. 5,893,875 discloses a surgical instrument with replaceable end effector assemblies. To switch between tissue cutting and grasping procedures, however, the surgeon must withdraw the instrument from the patient and replace the scissors end effector assembly with a forceps end effector assembly. This practice of instrument exchange greatly increases the time it takes to complete a given surgical procedure.

An attempt to overcome this problem is disclosed by a combined cutting blade/forceps end assembly. See U.S. Pat. Nos. 5,456,684 and 5,908,420. In another prior art device, a cutting blade is extendable between two forceps. See U.S. Pat. Nos. 5,496,317 and 5,573,535. See also the BiCoag® bipolar cutting forceps available from Everest Medical, 13755 First Avenue North, Minneapolis, Minn. 55441-5454.

All of these devices suffer from the fact that the scissoring and grasping capabilities are poorer than that which is available separately in single function devices.

Moreover, surgeons will not generally use any surgical instrument which does not operate in the way expected or in a way which is not intuitive. When conventional surgical devices with scissor grips are used, it is expected that the action of closing the scissor grips closes the scissor blades for tissue cutting or brings the forceps jaws together to grasp the tissue between them. This is not the case with the devices discussed above. For example, in order to use the device disclosed in U.S. Pat. No. 5,573,535, the surgeon uses a scissor grip to operate the forceps jaws but must operate a separate lever to effect distal movement of the blade member to cut tissue. See the '535 patent, col. 5, lines 43–66.

Other shortcomings of prior art devices include their complexity and high manufacturing costs. High manufacturing costs are especially important in surgical devices because they are often used in connection with one procedure on a given patient and then discarded.

Still another problem associated with the prior art is the non-ergonomic nature of the handle assembly associated with certain prior art surgical instruments. Surgeons are reluctant to use any surgical instrument whose operation is not fairly self-evident, or is complex, and/or is not similar to the operation of previously used surgical instruments. Also, surgeons desire a surgical instrument which provides feedback—a positive indication that it is working as intended.

In one prior art example, U.S. Pat. No. 5,403,322, incorporated herein by this reference, discloses a tissue approximator having two pivoting tissue grasping jaws each of which close about a central plate. The handle assembly of this device includes left and right pivoting triggers: the left trigger operates one tissue grasping jaw and the right trigger operates the other tissue grasping jaw.

The structure of this handle assembly is completely different from typical prior art laparoscopic instruments which typically include a scissor type handle with a pivoting trigger spaced from a fixed trigger. Surgeons, however, familiar with scissor type handle assemblies, are reluctant to use laparoscopic instruments with non-scissor type handles.

SUMMARY OF THE INVENTION

It is therefore an object of this invention to provide a surgical instrument which operates in the way expected and the use of which is intuitive.

It is a further object of this invention to provide such a surgical instrument which does not require the surgeon to operate separate levers in order to effect tissue cutting or tissue grasping procedures.

It is a further object of this invention to provide a surgical instrument with a handle assembly whose operation is self-evident, simple, and similar to the operation of previously used surgical instruments.

It is a further object of this invention to provide such a surgical instrument a handle assembly which provides a positive indication that it is operating as intended.

It is a further object of this invention to provide such a surgical instrument handle assembly which, in one embodiment, comprises an end effector assembly with a pivoting scissor blade and a pivoting tissue grasping jaw, which locks the scissor blade closed when the tissue grasping jaw is operated and, conversely, which locks the tissue grasping jaw closed when the scissor blade is operated.

It is a further object of this invention to provide such a surgical instrument in which although the tissue grasping jaw is locked closed when the scissor blade is operated, any tissue between the locked closed tissue grasping jaw can escape therefrom if the laparoscopic instrument is moved.

It is a further object of this invention to provide such a surgical instrument which is designed to allow operation of the switching mechanism independent of the drive mechanism so a surgeon can switch between the various modes of operation independent of the position of the pivoting jaws.

It is a further object of this invention to provide a surgical instrument with an end effector assembly which may include a pivoting scissor blade and a pivoting forceps jaw and also other types of surgical end effector assemblies.

It is a further object of this invention to provide such a surgical instrument which eliminates the need for the surgeon to switch instruments during a given medical procedure.

It is a further object of this invention to provide such a surgical instrument which eliminates the need for additional cannulas inserted through a patient's abdominal wall.

It is a further object of this invention to provide such a surgical instrument in which the scissoring and the grasping capabilities are as good as that which is available separately in single function devices.

It is a further object of this invention to provide such a surgical instrument which is simple in design and which can be manufactured at a low cost.

It is a further object of this invention to provide such a surgical instrument which allows surgeons to remain focused on the operating procedure and not distracted by instrument exchanges or the need to operate separate levers.

It is a further object of this invention to provide such a surgical instrument which results in medical procedures performed in a shorter period of time.

It is a further object of this invention to provide such a surgical instrument which can be accommodated by a five millimeter cannula.

It is a further object of this invention to provide such a surgical instrument which can be easily and ergonomically operated by one hand.

It is a further object of this invention to provide such a surgical instrument which can be equipped with bipolar or monopolar RF energy subsystems for electrosurgical procedures.

It is a further object of this invention to provide such a surgical instrument which can be readily equipped with surgical end effector assemblies other than scissors and tissue graspers.

It is a further object of this invention to provide a surgical instrument with an end effector assembly that may be rotated relative to its handle.

This invention results from the realization that a more intuitive, ergonomic, easier to use, and easier to manufacture surgical instrument which performs, in one example, both tissue cutting and grasping procedures without the need to replace the end effector assembly and which incorporates both scissors and forceps (or other end effector combinations) jaws in a single end effector assembly can be effected by a uniquely configured end effector assembly with a fixed central member that functions both as a scissor blade and a forcep jaw disposed between a separate pivotable scissor blade and a separate pivotable forcep jaw and by a linkage assembly connected between the end assembly and a pair of scissors grips which allows the surgeon to operate the scissor blade when the switching mechanism is in a first position and which allows the surgeon to operate the tissue grasping jaw is when the switching mechanism is in a second position. Moreover, the switching mechanism automatically locks the pivoting scissor blade closed when the tissue grasping jaw is being used and, conversely, the switching mechanism automatically locks the pivoting tissue grasping jaw closed when the pivoting scissor blade is being used. In addition, the switching mechanism can be placed in either the first or second position independent of the position of either the pivoting scissor blade or the pivoting tissue grasping jaw. The result is an ergonomic, easy to use, multi-function laparoscopic instrument which provides positive feedback to the surgeon regarding whether the pivoting tissue grasping jaw is operable or, instead, the pivoting scissor blade is operable.

This invention features a multi-function surgical instrument (e.g., a laparoscopic) comprising an end effector assembly including at least first and second movable members, a first actuator coupled to the first movable member, a second actuator coupled to the second movable member, and a handle assembly. In the preferred embodiment, the handle assembly includes a drive mechanism and a switching mechanism coupled to the drive mechanism. The switching mechanism has at least two positions: a first position in which the drive mechanism is engaged with the first actuator to operate the first movable member and a second position in which the drive mechanism is engaged with the second actuator to operate the second movable member.

Typically, the handle assembly further includes at least one movable trigger pivotably coupled to the drive mechanism. The end effector assembly may include a stationary member between the first and second movable members. In one embodiment, the stationary member has a cutting blade surface and a tissue grasping surface and the first movable member includes a cutting blade surface which cooperates with the cutting blade surface of the stationary member. The second movable member then includes a tissue grasping surface which cooperates with the grasping surface of the stationary member. In one example, the first and second actuators are lengthy rods extending between the end effector assembly and the handle assembly for laparoscopic procedures. A sheath may surround the lengthy rods.

In the preferred embodiment, a first coupler is disposed on the proximal end of the first actuator and a second coupler is disposed on the proximal end of the second actuator. Both couplers are configured to be engaged by the drive mechanism. The first and second couplers each typically include a circumferential groove therein which is engageable by the drive mechanism independent of the rotational orientation of the first and second couplers. The first coupler may also include a passageway which slidably receives the second actuator therethrough and thus the second coupler is positioned rearward of the first coupler in the handle assembly.

The drive mechanism may include a forward clamp engageable with the first coupler and a rearward clamp engageable with the second coupler. In this design, the first coupler includes spaced bushings on opposite sides of the circumferential groove and the forward clamp of the drive mechanism includes a fork-like construction with an opening which receives the circumferential groove of the first coupler therein when the drive mechanism is pivoted to engage the first coupler. Similarly, the second coupler typically includes spaced bushings on opposite sides of the circumferential groove and the rearward clamp of the drive mechanism then includes a fork-like construction with an opening which receives the circumferential groove of the second coupler therein when the drive mechanism is pivoted to engage the second coupler. The handle assembly may further include a stationary trigger spaced forward from the movable trigger.

In the preferred embodiment, the switching mechanism includes at least a first button and a rocking member pivotable between a first position which urges the drive mechanism to engage the first actuator and a second position which urges the drive mechanism to engage the second actuator. The rocking member may include a first locking member which engages the first actuator when the drive mechanism is engaged with the second actuator and a second locking member which engages the second actuator when the drive mechanism is engaged with the first actuator. In one example, the rocking member includes an arm and the switching mechanism further includes a first spring disposed between the first button and the arm of the rocking member which urges the arm in a first direction when the first button is depressed. The first button may also include a pawl which pulls the arm forward when the first button moves from a depressed position to an outward position. In this preferred embodiment, the switching mechanism further includes a second spring which biases the first button in the outward position to urge the arm of the rocking member in a second direction when the first button is released. The switching mechanism may further include a catch which holds the first button in the depressed position and a second button which, when depressed, releases the catch and the first button. The second button is typically biased outward.

It is preferred that the switching mechanism further includes a lock-out subsystem configured to engage the first actuator when the drive mechanism engages the second actuator and to engage the second actuator when the drives mechanism engages the first actuator. Also, a voltage supply lead may be included and electrically connected to one of the first and second movable members for coagulating tissue. The voltage supply lead may be attached to the first actuator and insulation provided to surround the first actuator. A second voltage supply lead may be attached to the second actuator.

The preferred switching mechanism includes a pivotable rocker assembly including a depending arm and forward and rearward shelves which alternately engage the drive mechanism. An actuator is coupled to the depending arm of the rocker assembly. The actuator may be a button including a spring which is disposed to push on the arm of the rocker assembly when the button is depressed, the button further including a pawl biased to pull the arm of the rocker assembly when the button is released. In the preferred embodiment, the pivotable rocker assembly further includes forward and rearward stops disposed to engage whichever actuator is not engaged by the drive mechanism.

This invention further features a multi-function laparoscopic instrument comprising an end effector assembly including at least first and second movable jaws, a first actuator coupled to the first movable jaw, a second actuator coupled to the second movable jaw, a drive mechanism engageable with the first and second actuators and switching means having a first position which orients the drive mechanism to engage the first actuator and a second position which orients the drive mechanism to engage the second actuator for alternatively operating the first and second movable jaws.

Typically, the first and second movable jaws have a neutral position and the switching means is configured to force the drive mechanism to engage the first or second actuator only when the movable jaws are in the neutral position. The drive mechanism may be pivotable forward to engage the first actuator and pivotable rearward to engage the second actuator. The switching means may include a rocker member pivotable in one direction to urge the drive mechanism to pivot forward and pivotable in another direction to urge the drive mechanism to pivot rearward. The rocker member may include an arm and the switching means then further includes a first button and a compliant member between the first button and the arm to bias the arm of the rocker in a first direction independent of the position of the drive mechanism. The switching means may further include a pawl attached to the first button and a second compliant member disposed to bias the arm of the rocker in a second direction independent of the position of the drive mechanism.

The switchable actuator assembly of this invention typically includes a first actuator, a second actuator, a forward coupler attached to the proximal end of the first actuator and having a passage which receives the second actuator therethrough, a rearward coupler on the proximal end of the second actuator, a pivotable drive mechanism disposed over the forward and rearward couplers, and a switching mechanism engageable with the pivotable drive mechanism for pivoting the drive mechanism rearward to engage the rearward coupler and forward to engage the forward coupler. The switching mechanism includes a rocker member pivotable in a first direction to urge the drive mechanism to pivot rearward and pivotable in a second direction to urge the drive mechanism to pivot forward. The switching mechanism further includes an actuator compliantly coupled to the rocking member and operable independent of the position of the first and second actuators.

In the preferred embodiment, the rocker member includes a forward shelf which urges the drive mechanism to pivot rearward and a rearward shelf which urges the drive mechanism to pivot forward. Also in the preferred embodiment, the rocker member includes a forward locking member which holds the forward coupler stationary when the drive mechanism is engaged with the rearward coupler and a rearward locking member which holds the rearward coupler stationary when the drive mechanism is engaged with the forward coupler. The rocker member may include an arm and there may be a first spring extending between the first actuator and the arm to urge the arm rearward when the actuator is in a first position. The actuator may further include a pawl which urges the arm forward when the actuator is in a second position and a second spring which biases the actuator in the second position.

Typically, the actuator is a first button, the first position is depressed and the second position is released. The switching mechanism may further include a second button which locks the first button in the depressed position and which is itself depressible to release the first button.

In the preferred embodiment, there is an end effector assembly including a central fixed jaw with a grasping surface and a cutting surface, a first movable jaw including a grasping surface which engages the grasping surface of the central fixed jaw to grasp tissue therebetween as the first movable jaw is opened and closed. A second movable jaw includes a cutting surface which cooperates with the cutting surface of the central fixed jaw to cut tissue therebetween as the second movable jaw is opened and closed. A first actuator has a distal end coupled to the first movable jaw and reciprocates to open and close the first movable jaw. A second actuator has a distal end coupled to the second movable jaw and reciprocates to open and close the second movable jaw. There is also a handle assembly including the proximal ends of both the first and second actuators, a drive mechanism having a first position which engages the proximal end of the first actuator and a second position which engages the proximal end of the second actuator, and a movable trigger coupled with the drive mechanism to open and close the first movable jaw when the drive mechanism is engaged with the proximal end of the first actuator and to open and close the second movable jaw when the drive mechanism is engaged with the proximal end of the second actuator. The exemplary handle assembly further includes a switching mechanism coupled to the drive mechanism to switch it between the first and second positions.

The switching system, in one embodiment of this invention, features a pivotable drive mechanism translatable forward and rearward, a movable handle pivotable about a first pin and pivotably connected to the drive mechanism by a second pin, a rocker assembly pivotably disposed about the first pin and including a forward shelf which urges the drive mechanism to pivot in a first direction and a rearward shelf which urges the drive mechanism to pivot in a second direction. The rocker assembly may further include an arm depending therefrom. An actuator has first and second positions and includes a first compliant member (e.g., a spring) which urges the arm of the rocker assembly rearward when the actuator is in the first position to pivot the rocker assembly to engage the rearward shelf thereof with the drive mechanism. The actuator may further include a pawl which urges the arm of the rocker assembly forward when the actuator is in the second position to pivot the rocker assembly to engage the forward shelf thereof with the drive mechanism.

In one example, the actuator is a button depressible to the first position and releasable to the second position. A second compliant member is included, typically a spring, which biases the actuator in the second position.

BRIEF DESCRIPTION OF THE DRAWINGS

Other objects, features and advantages will occur to those skilled in the art from the following description of the preferred embodiment and the accompanying drawings, in which.

DISCLOSURE OF THE PREFERRED EMBODIMENT

Figure 1:
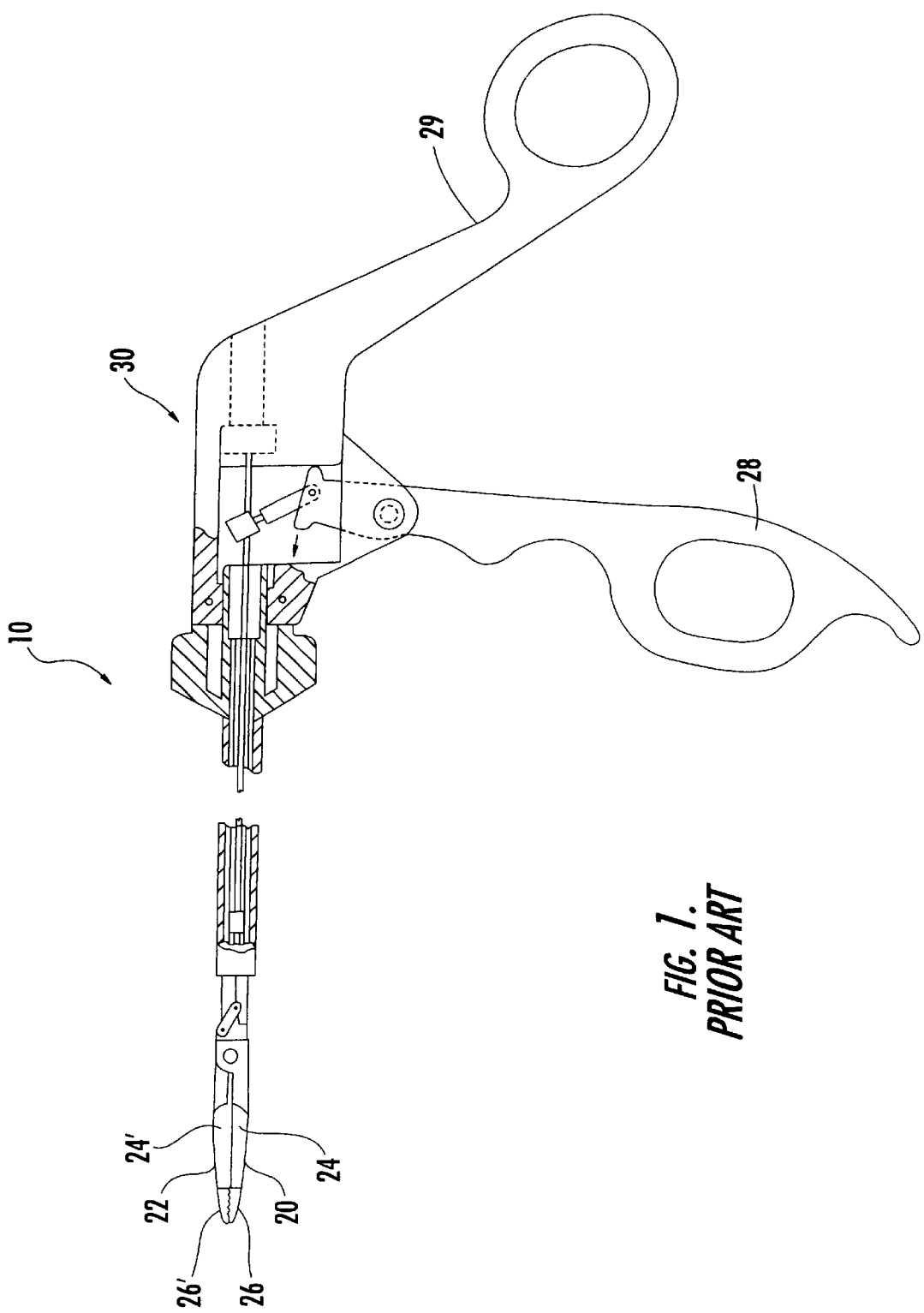
FIG. 1 is a schematic partial cutaway view of a prior art multi-function laparoscopic instrument with a scissor type handle assembly.

FIG. 1 shows prior art laparoscopic instrument 10 including pivoting jaws 20, 22 each of which includes a scissor blade portion 24,24' and a tissue grasping portion 26,26'. As delineated in the Background section above, the cutting and tissue grasping capabilities of this device are poorer than that which is available in single function (cuffing or tissue grasping) devices. Still, laparoscopic instrument 10 includes handle assembly 30 including pivoting scissor type handle 28 spaced from fixed scissor type handle 29 and, thus handle assembly 30 is, to some extent, ergonomic in design and also a design with which surgeons are familiar.

Figure 2:
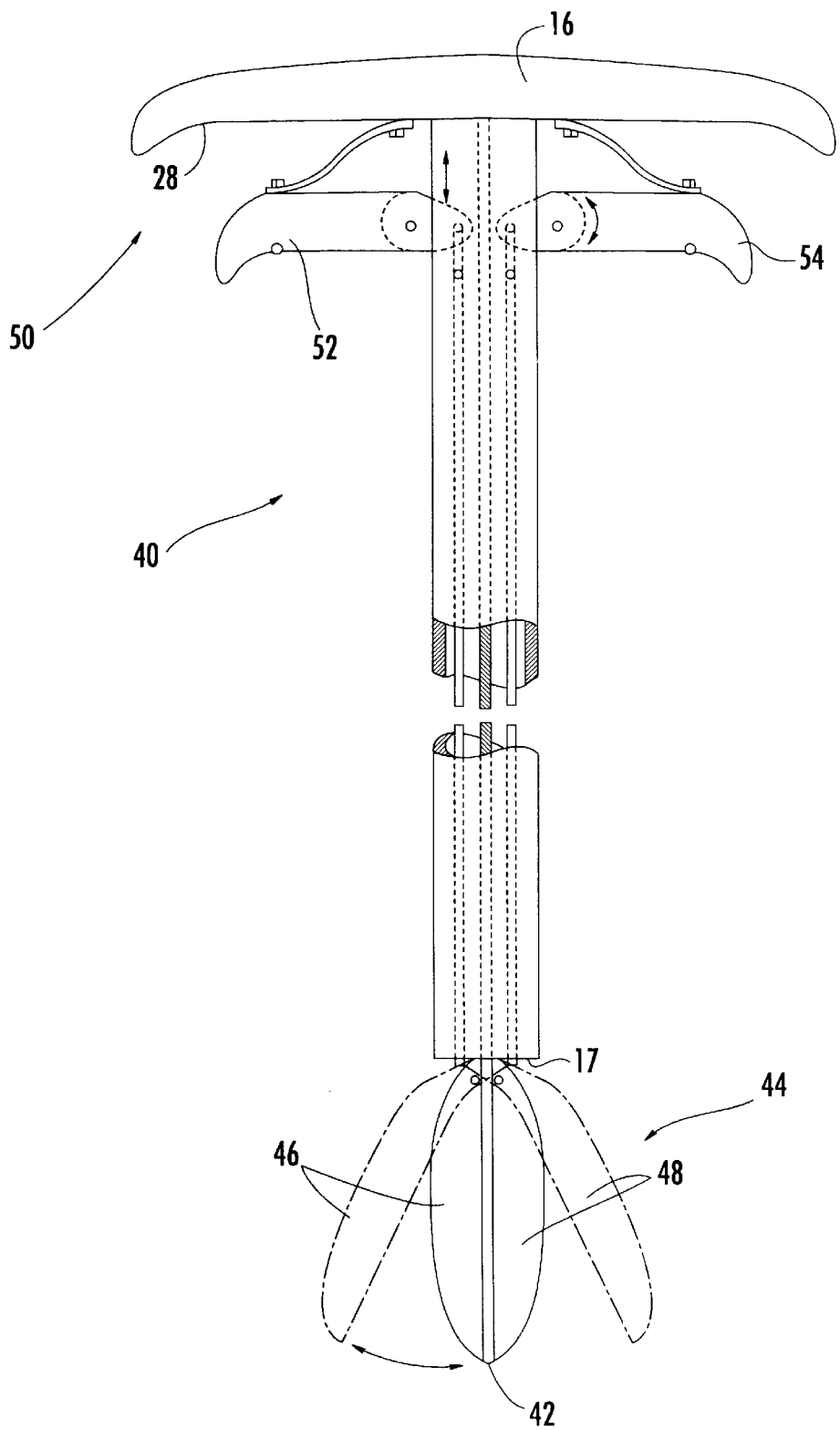
FIG. 2 is a schematic view of a prior art tissue approximator including a non-scissor type handle assembly.

The end effector assembly 44 of tissue approximator 40, FIG. 2 includes central plate 42 and pivoting tissue grasping jaws 46 and 48 which close about central plate 42. Tissue approximator 40 is not a dual function device, however, since no tissue cutting operations can be performed, and, worse, handle assembly 50 wherein left pivoting handle 52 operates jaw 46 and right pivoting handle 54 operates jaw 48 constitutes a serious departure from the design of scissor type handles (see FIG. 1) previously used by surgeons.

In this invention, the overall design of a scissor type handle assembly—the operation of which is known to surgeons—is maintained and yet, at the same time, the laparoscopic surgical instrument of this invention, in the preferred embodiment, provides dual functionality.

Figure 3:
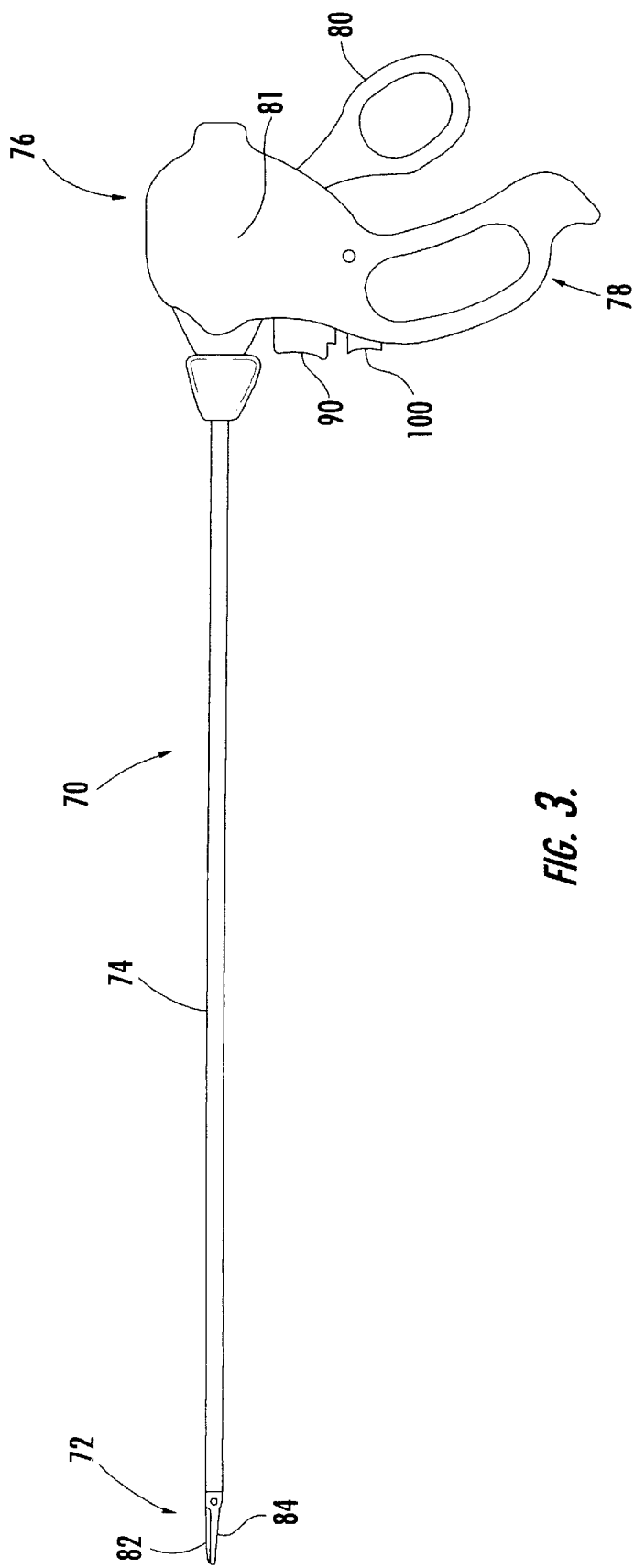
FIGS. 3–4 are schematic views of one example of a multi-function laparoscopic instrument of the subject invention showing the operation of the pivoting scissor blade when the switching mechanism is in a first position.

As shown in FIG. 3, laparoscopic instrument 70 includes end effector assembly 72, shaft sheath 74, and handle assembly 76 with fixed forward trigger 78 and rearward trigger 80 movable with respect to handle housing 81. In other designs, trigger 78 could be movable and trigger 80 fixed or, instead, both of the triggers could be movable.

End effector assembly 72 includes, in this example, first movable member 82 and second movable member 84. In this particular example, first movable member 82 is a pivoting scissor blade and second movable member 84 is a pivoting tissue grasping jaw as delineated in co-pending U.S. patent application Ser. No. 09/519,103 incorporated herein by this reference.

In other examples, end effector assembly 72 includes two pivoting tissue grasping jaws, two pivoting scissor blades, needle holder and cutter combinations, and also other known surgical instrument end effector assemblies. In the following disclosure, the particular end effector assembly disclosed in co-pending U.S. patent application Ser. No. 09/519,103 is used as an example but this example is not intended to limit the scope of the invention disclosed herein.

Figure 4:
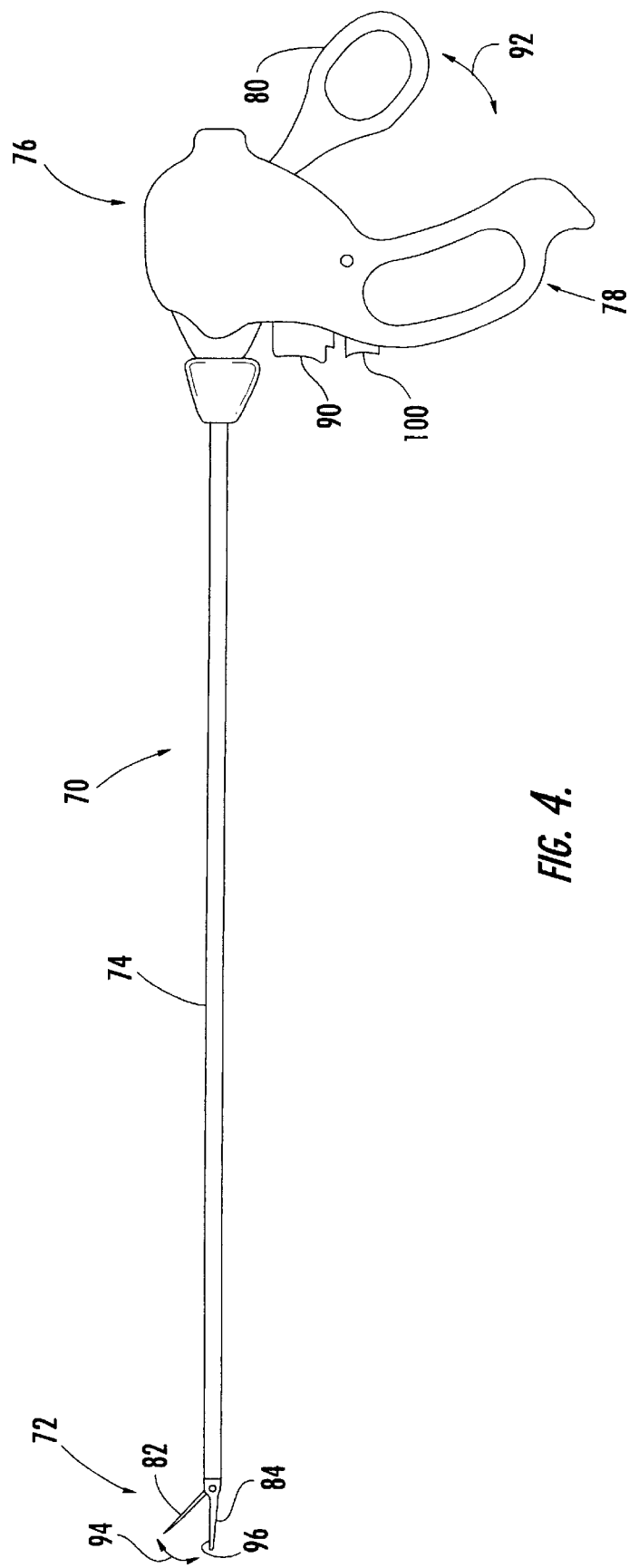

In FIGS. 3–4, button 90 of the handle assembly 76 is not depressed. In this position, handle or trigger 80 pivots in the direction shown by arrow 92, FIG. 4 to operate pivoting scissor blade 82 in the direction shown by arrow 94 to cut tissue between pivoting scissor blade 82 and stationary or fixed member 96, the upper surface of which includes a blade which cooperates with pivoting scissor blade 82.

Figure 5:
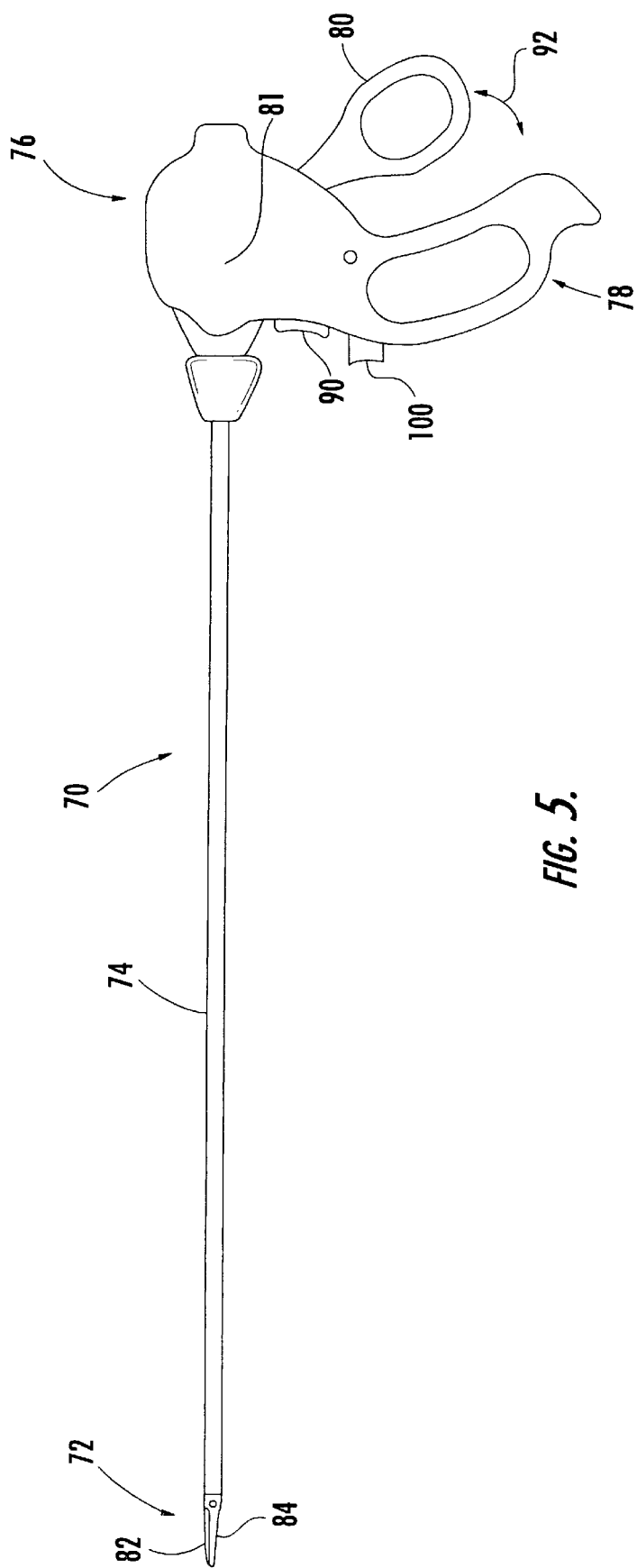
FIGS. 5–6 are schematic views of the multi-function laparoscopic instrument of FIGS. 3–4 showing the operation of the pivoting tissue grasping jaw when the switching mechanism is in a second position.

To then grasp tissue or to coagulate tissue, the surgeon depresses button 90 as shown in FIG. 5. Then, as the movable trigger or handle 80 is actuated in the direction shown by arrow 92, FIG. 6, second movable member 84 (in this example, a tissue grasping jaw) operates (pivots) in the direction shown by arrow 98. In this particular example, the lower surface of stationary or fixed member 96 includes a tissue grasping surface which cooperates with pivoting tissue grasping jaw 84. When button 100 is depressed, button 90 is released as shown in FIGS. 3–4 and further tissue cutting operations may then be performed. In other embodiments, the operation of button 90 may be reversed: depressing button 90 operates the scissor blade 82 and releasing button 90 operates tissue grasping jaw 84.

One feature of this invention is that when tissue cutting operations are being performed as shown in FIGS. 3–4, pivoting tissue grasping jaw 84 remains closed but, preferably, the pressure exerted by pivoting tissue grasping jaw 84 against fixed member 96 is very low and thus any tissue therebetween can easily slide out ensuring that if the surgeon moves laparoscopic instrument 70 to perform cutting or other operations, tissue is not inadvertently grasped between pivoting tissue grasping jaw 84 and fixed member 96.

Figure 6:
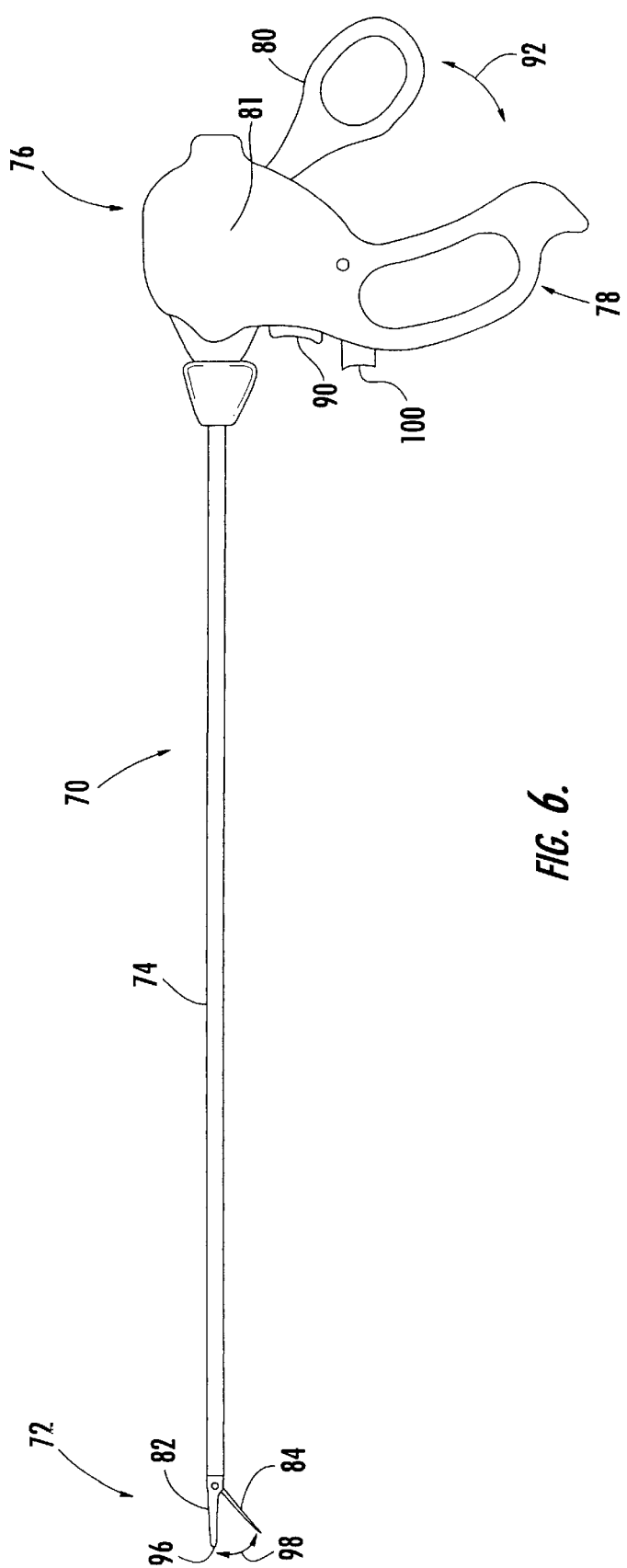

Similarly, when tissue grasping jaw 84 is being used to perform tissue grasping or coagulating operations as shown in FIGS. 5–6, pivotable scissor blade 82 remains closed against fixed member 96 (see FIG. 6) to prevent unintended piercing or cutting of tissue.

Still another feature of the subject invention is the fact that button 90 can be depressed or released independent of the position of pivoting scissor blade 82 or pivoting tissue grasping jaw 84. Thus, the surgeon can switch between tissue grasping or coagulating procedures and cutting procedures at any time independent of the position of pivoting handle 80 and also independent of the position of pivoting scissor blade 82 and pivoting tissue grasping jaw 84. Thus, the surgeon can depress button 90 even when scissor blade 82 is fully open as shown in FIG. 4 and the surgeon can also release button 90 (by pushing button 100) even when tissue grasping jaw 84 is fully open as shown in FIG. 6.

A corollary feature of this invention is the fact that when button 90 is depressed, scissor blade 82, FIG. 4 automatically closes (see FIG. 5) when handle 80 is moved and, conversely, when button 90 is released by button 100, tissue grasping jaw 84, FIG. 6 automatically closes when handle 80 is moved (see FIG. 3).

These features result in a laparoscopic or other surgical instrument which is ergonomic in design, easy and in fact self-evident to use, safe, and which provides positive feedback to the surgeon who, upon depressing button 90 or, alternatively, by depressing button 100 to release button 90, is ensured that the corresponding and intended operation of end effector assembly 72 is effected: depressing button 90 allows the operation of pivotable scissor blade 82 via handle 80 and depressing button 100 (which releases button 90) allows the operation of pivoting tissue grasping jaw 84 via handle 80. In one example, laparoscopic instrument 70, FIGS. 3–6 has shaft 74 which is 33 cm long and 5 mm in diameter. Tissue grasping jaw 84, scissor blade 82, central member 96, and actuating rods 110 and 112, FIG. 7 may be made of stainless steel, for example while the other components of the instrument of this invention are typically plastic.

Figure 7:
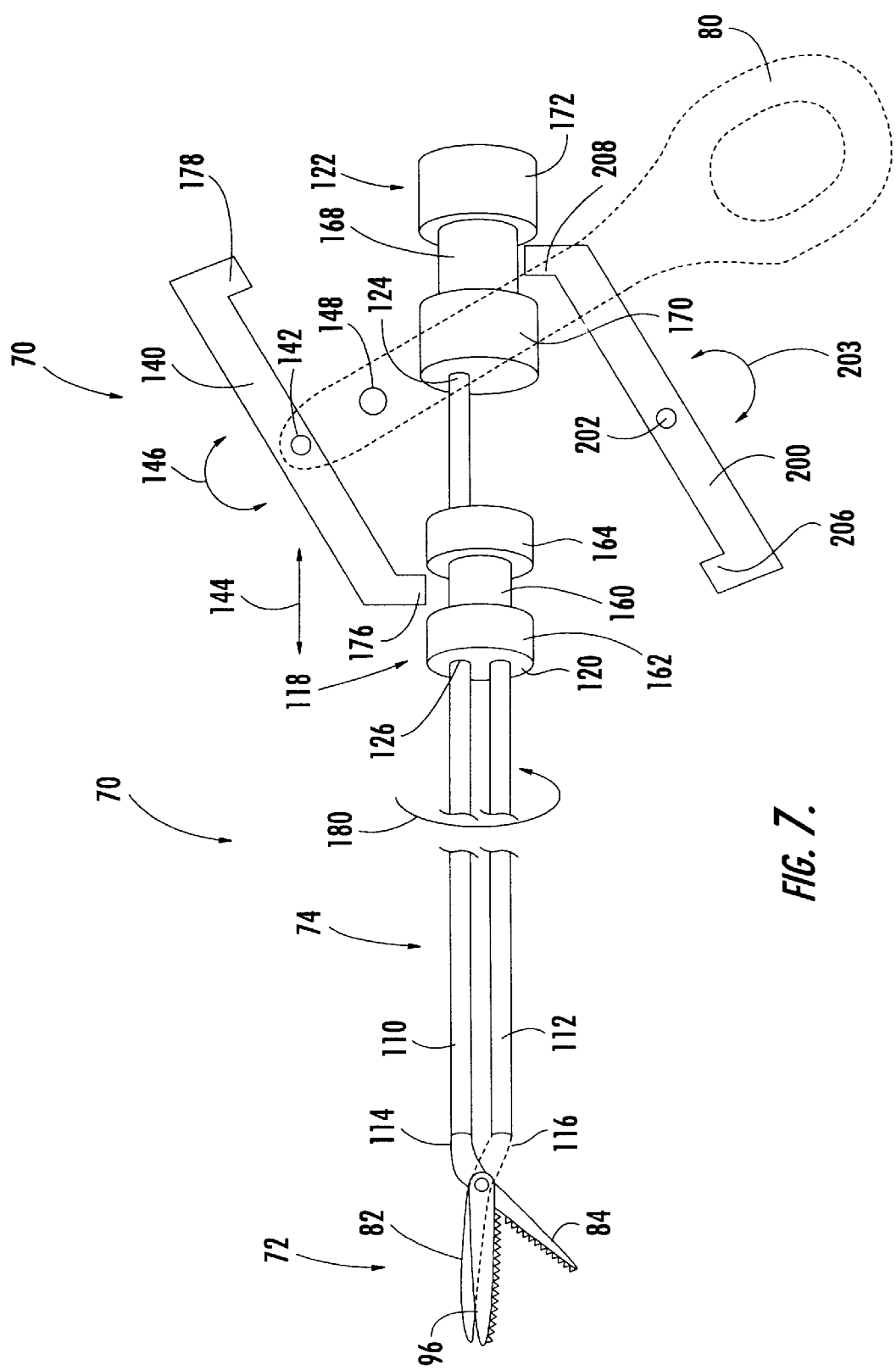
FIG. 7 is a highly schematic view of the drive mechanism and the lockout mechanism in one example of the subject invention.

FIG. 7 schematically depicts the operation of several components associated with the preferred embodiment of laparoscopic instrument 70. Lengthy actuator rod 112 is coupled on distal end 116 to pivoting scissor blade 82 and extends to first, forward coupler 118 at proximal end 120 inside handle assembly 70, FIGS. 3–6. Lengthy actuator rod 110, FIG. 7 is coupled to pivoting tissue grasping jaw 84 at distal end 114 and extends to second, rearward coupler 122 at proximal end 124 passing slidably through orifice 126 in first forward coupler 118.

In FIG. 7, sheath 74, FIGS. 3–6 is not shown. Also, in FIG. 7, other components associated with handle assembly 70 are not shown to focus on one example of drive mechanism 140 and also one example of locking device 200.

Drive mechanism 140 pivots about pin 142 as shown by arrow 146 but is also disposed inside handle assembly 76, FIGS. 3–6 to reciprocate forward and rearward as shown by arrow 144, FIG. 7 by virtue of movable trigger 80 which is pivotably coupled to drive mechanism 140 at pivot pin 142. Movable trigger 80 pivots about pin 148 fixed inside handle assembly 76, FIGS. 3–6.

In this way, drive mechanism 140 can be pivoted forward as shown in FIG. 7 to engage coupler 118, and, when so engaged, handle 80 can be operated to move drive mechanism 140 forward and rearward to open and close tissue grasping jaw 84. Since actuator rod 110 passes slidably through forward coupler 118, actuator rod 110, rearward coupler 122, and scissor blade 82 do not move when forward coupler 118 is driven forward and rearward by drive mechanism 140 and handle 80.

Drive mechanism 140 can also be pivoted rearward to engage coupler 122 and then, as handle 80 is operated to move drive mechanism 140 forward and rearward, pivoting scissor blade 82 is opened and closed. Again, since actuator rod 110 passes slidably through forward coupler 118, forward coupler 118, actuator rod 112, and tissue grasping jaw 84 do not move when drive mechanism 140 engages rearward coupler 122 and handle 80 is used to move drive mechanism 140 forward and rearward to open and close scissor blade 82.

Thus, in general, drive mechanism 140 has two positions: a first position in which drive mechanism 140 is engaged with the actuator which operates a first movable end effector member when movable trigger 80 is activated and a second position in which drive mechanism 140 is engaged with another actuator to operate a second end effector movable member when movable trigger handle 80 is activated.

As shown in FIG. 7, forward coupler 118 includes circumferential groove 160 therein between bushing surfaces 162 and 164. Similarly, rearward coupler 122 includes circumferential groove 168 between bushing surfaces 170 and 172. Circumferential groove 160 of forward coupler 118 receives forward clamp 176 of drive mechanism 140 and circumferential groove 168 of rearward coupler 122 receives rearward clamp 178 of drive mechanism 140. This construction of the couplers results in two distinct features: first, the spaced bushings of each coupler provide a positive engagement with the drive mechanism as it is driven forward and rearward and, second, allows end effector assembly 72, actuator rods 110 and 112, and forward 118 and rearward 122 couplers to be rotated as shown by arrow 180 independent of drive mechanism 140, independent of the other components inside handle assembly 76, FIGS. 3–6, and also independent of the handle assembly housing itself.

As explained above, one feature of the subject invention is that the scissor blade remains closed when tissue grasping jaw 84 is operable to open and close and, conversely, the tissue grasping jaw is locked closed when the scissor blade is operable. Thus, in the preferred embodiment, locking device 200, FIG. 7 is included inside handle assembly 76, FIGS. 3–6 and disposed therein to pivot about pin 202, FIG. 7 in the direction shown by arrow 203. Locking device 200 may thus include forward locking member 206 which engages coupler 118 when locking device 200 is pivoted in one direction and also includes rearward locking member 208 which engages coupler 122 when locking device 200 is pivoted in the opposite direction.

Thus, in general, locking device 200 engages whichever coupler is not engaged by drive mechanism 140. Thus, locking device 200 prevents whichever end effector jaw that is not being used from interfering with the current procedure.

Figure 8:
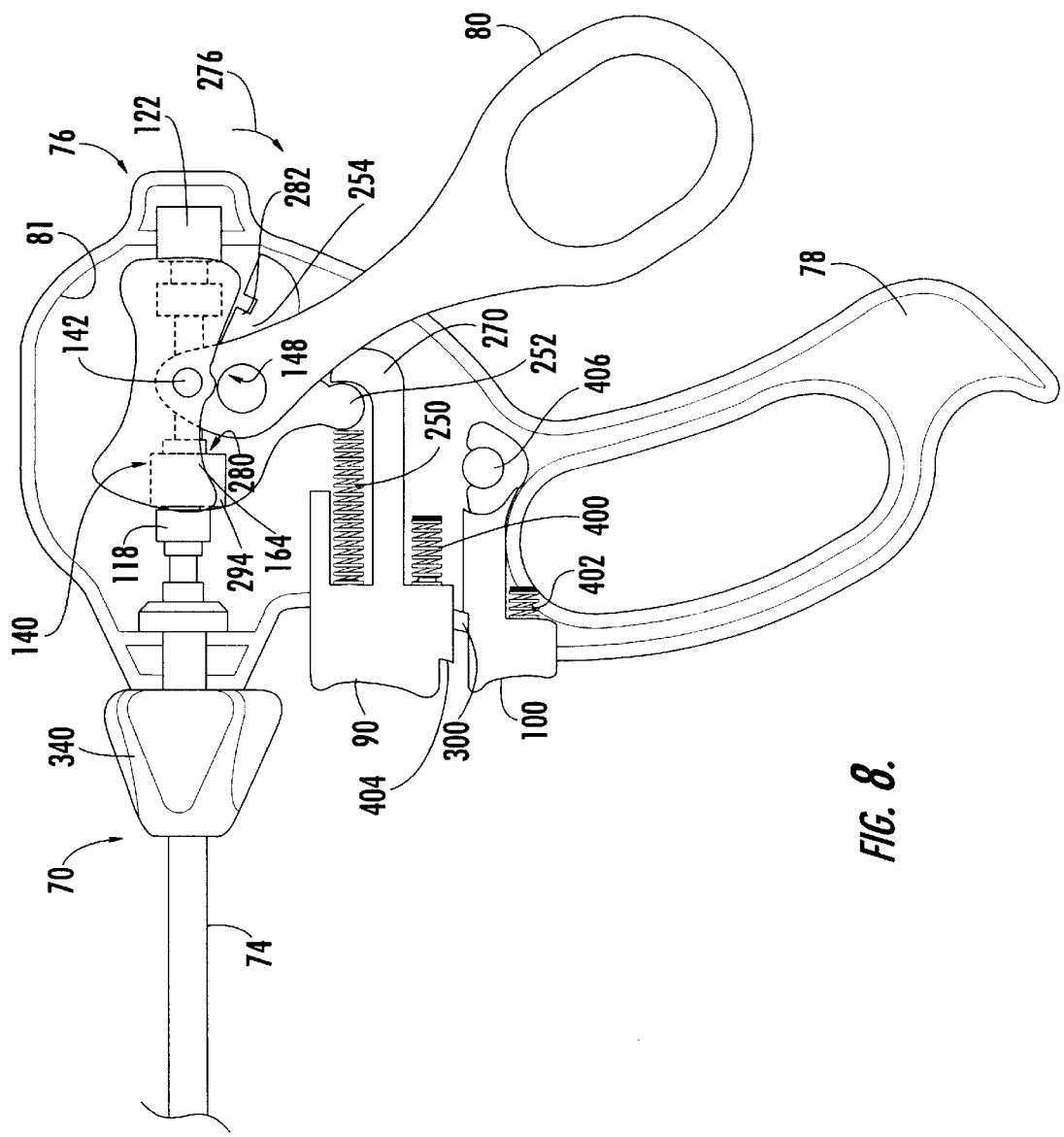
FIG. 8 is a more detailed schematic view showing the primary components associated with the handle assembly of the preferred embodiment of the multi-function surgical instrument of the subject invention when the push button is released.

As delineated above, FIG. 7 is highly schematic. In the preferred embodiment, the mechanism which causes drive mechanism 140 to switch between engagement with couplers 118 and 122 is integral with the locking mechanism as shown in FIG. 8.

Figure 9:
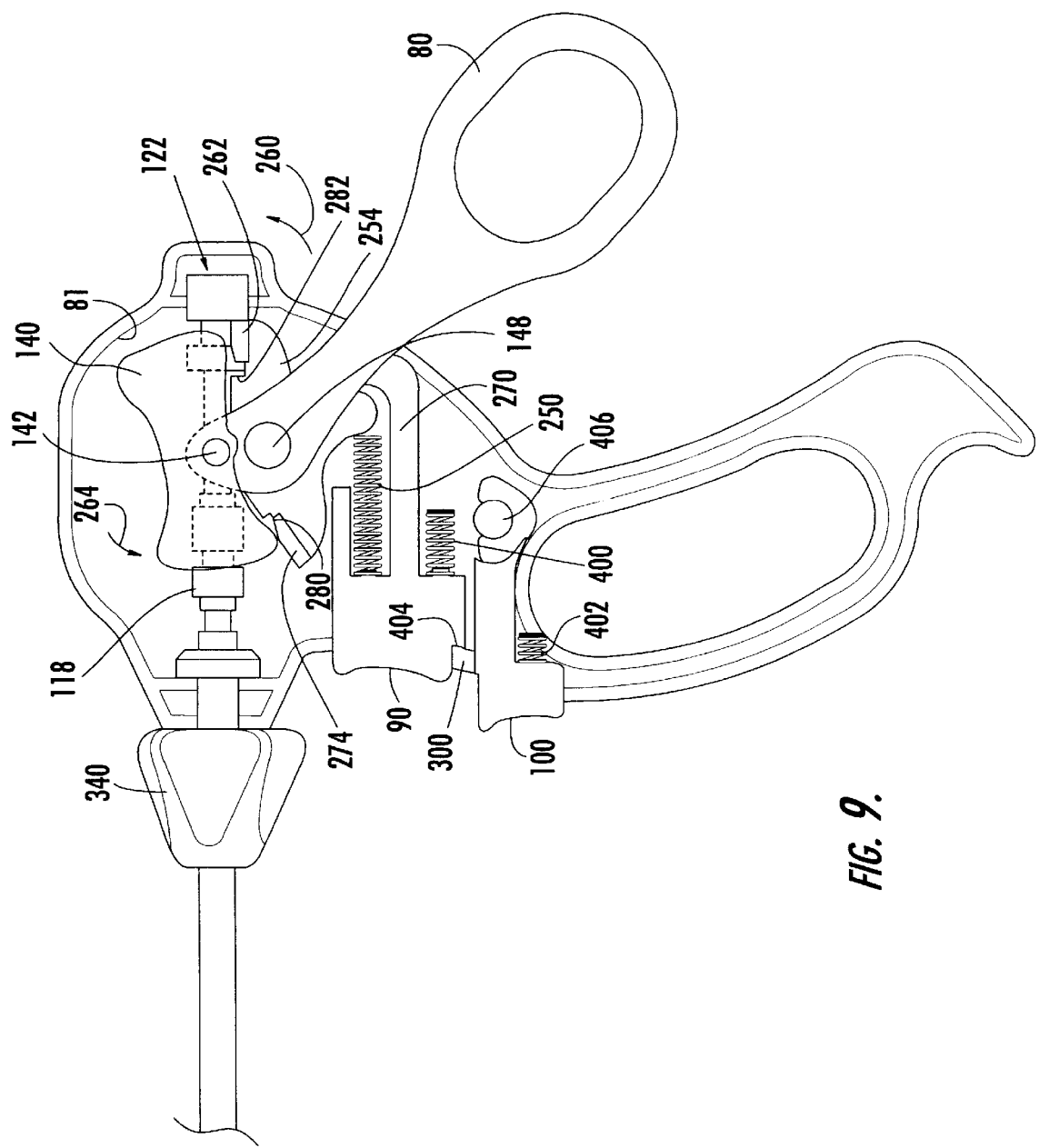
FIG. 9 is a view similar to FIG. 8 except now the push button of the handle assembly is depressed.

In this preferred embodiment, the switching mechanism includes the combination of button 90 indirectly and compliantly coupled to drive mechanism 140 via spring 250 which pushes arm 252 of rocking member 254 rearward when button 90 is depressed as shown in FIG. 9. Rocking member 254 pivots about pin 148 which is also the pivot point for handle 80. This causes rocking member 254 to pivot in the direction shown by arrow 260 whereupon shelf 262 of rocking member 254 urges drive member 140 to pivot in the direction shown by arrow 264 to engage forward coupler 118. Button 90 also includes pawl 270 which pulls arm 252 of rocking member 254 forward as shown in FIG. 8 when button 90 is released or outward as shown. This action causes rocking member 254 to pivot in the direction shown by arrow 276 which, in turn, drives shelf 274 of rocking member 254 upward urging drive mechanism 140 to engage rearward coupler 122. Moreover, rocking member 254 includes a lock-out subsystem as discussed above configured to engage coupler 118 when drive mechanism 140 is engaged with coupler 122 (FIG. 8) and to engage coupler 122 when drive mechanism 140 is engaged with coupler 118 (FIG. 9). In the preferred embodiment, this lock-out subsystem includes stop 280 which engages bushing 164 of coupler 118 (FIG. 8) and stop 282 which engages bushing 170 of coupler 122 (FIG. 9).

In this way, the switching mechanism including the combination of button 90, spring 250, and rocking member 254 accomplishes two functions: first, it moves drive mechanism 140 into alternate engagement with the two actuators via couplers 118 and 122 and, second, it locks the coupler not engaged by the drive mechanism.

Moreover, the use of spring 250 allows button 90 to be depressed and released independent of the position of couplers 118 and 122 and their corresponding actuator rods. Since button 90 can be depressed or released independent of the position of forward coupler 118 and independent of the position of rearward coupler 122, the surgeon can switch between tissue grasping or coagulating procedures and cutting procedures at any time irrespective of the position of pivoting handle 80 and also irrespective of the position of the pivoting jaw members included as part of the end effector assembly. A corollary feature of this invention is the fact that when button 90 is depressed, scissor blade 82, FIG. 3 closes when handle 80 is moved, and, conversely, when button 90 is released by button 100, tissue grasping jaw 84, FIG. 5 closes when handle 80 is moved.

These features result in a laparoscopic or other surgical instrument which is ergonomic in design, easy and in fact self-evident to use, safe, and which provides positive feedback to the surgeon who, upon depressing or releasing button 90 is ensured that the corresponding and intended operation of end effector assembly 72, FIGS. 3–6, is effected.

Although these features are important to the preferred embodiment of the subject invention, they are not critical in other embodiments of the subject invention. In other embodiments, those skilled in the art will understand how to engineer different kinds of switching and drive mechanisms and even actuators other than push buttons. Moreover, the mechanism which causes the drive mechanism to engage alternately the different actuators need not be integral with the lock-out mechanism.

Continuing with the preferred embodiment, second button 100 is disclosed with catch 300, FIG. 9 which locks button 90 in the depressed position. When button 100 is depressed, button 90 snaps outward as shown in FIG. 8. In other embodiments, a second button may not be required and button 90 could be self-lockable in the depressed position and self-releasable to the outward position.

Figure 10:
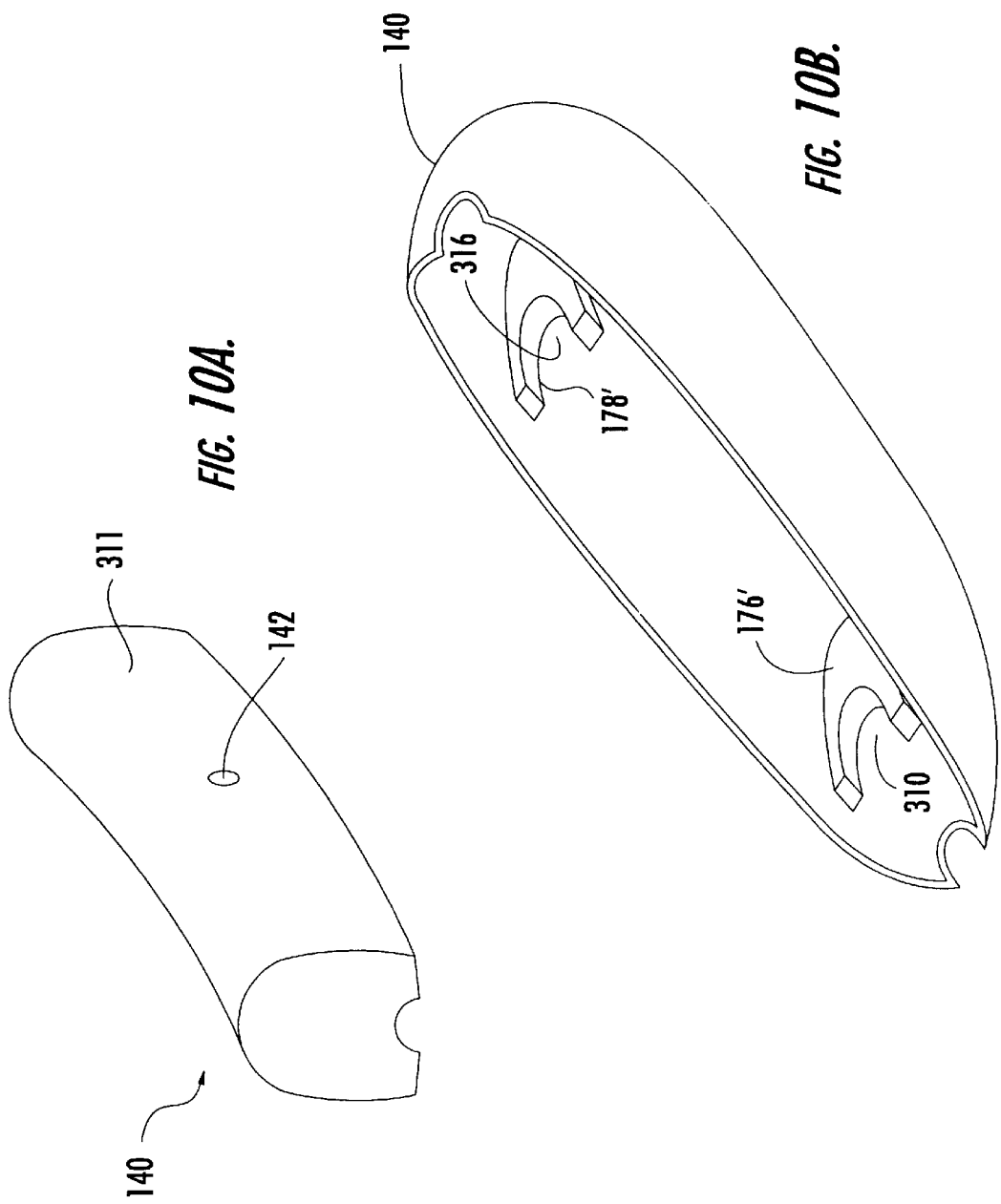
FIGS. 10A–10B are schematic views of one embodiment of the drive mechanism of the subject invention.

The preferred embodiment of drive mechanism 140 is shown in more detail in FIGS. 10A–10B. Forward clamp 176', FIG. 10B, includes opening 310 which receives and clamps on the central circumferential groove of forward coupler 118 when drive mechanism 140 is in the position shown in FIG. 9. Similarly, rearward clamp 178', FIG. 10 of the drive mechanism includes opening 316 which receives and clamps about the central circumferential groove of rearward coupler 122 when drive mechanism 140 is in the position shown in FIG. 8. This fork-like construction of clamps 176' and 178' engages the groove between the bushings of the couplers. As shown in FIG. 10A, the body of drive mechanism 140 is angled upward at rear portion 311 and drive mechanism 140, which pivots about pin 142, is thus able to alternatively engage and disengage the forward and rearward couplers.

Figure 11:
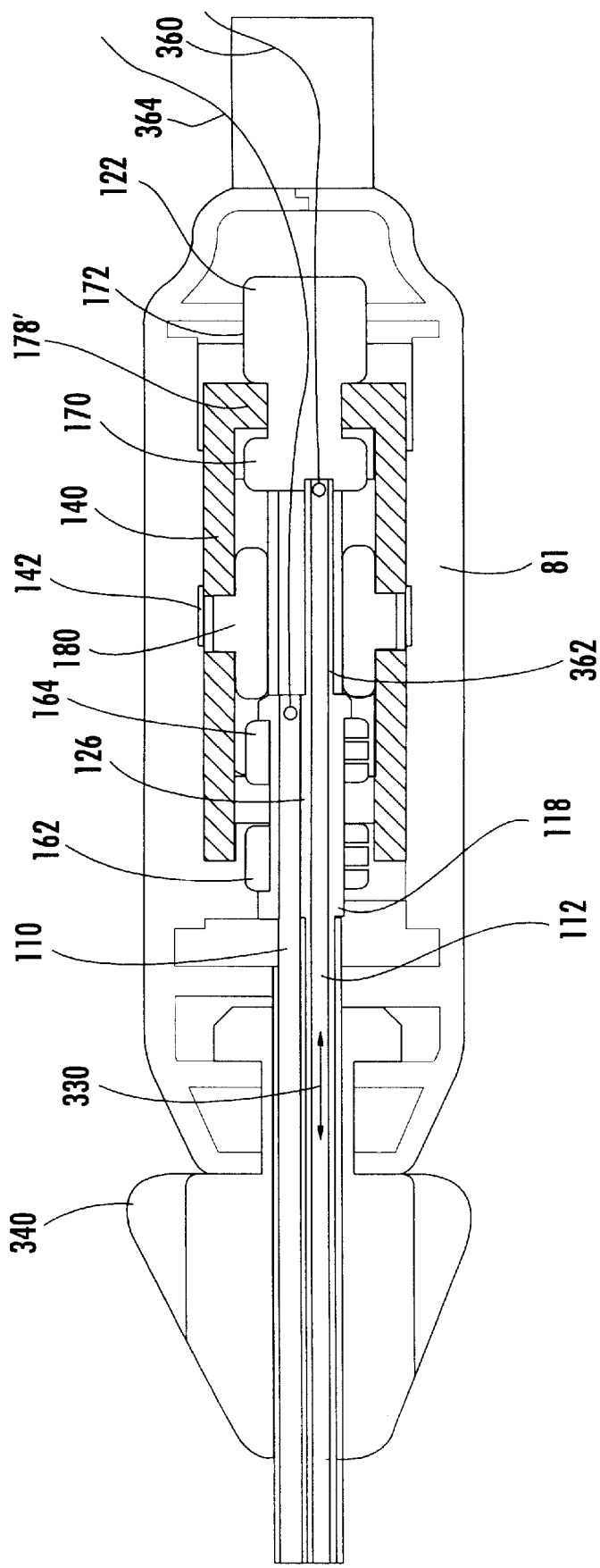
FIG. 11 is a cut-away top view of the preferred embodiment of the multi-function laparoscopic instrument of the subject invention.

FIG. 11 shows drive mechanism 140 in position clamped on coupler 122 and also shows how drive mechanism 140 is able to move inside handle assembly housing 81 forward and rearward to reciprocate actuator rod 112 back and forth as shown by arrow 330. Coupler 340 is used to rotate end effector assembly 72, FIG. 7 in the direction of arrow 180 as discussed above.

Voltage supply lead 360 may be included and connected to actuator rod 112 which is electrically insulated by protective covering 362. Furthermore, voltage supply lead 364 may also be included and connected to actuator rod 110 for bipolar coagulating operations. Alternatively, only one member of the end effector may be electrically connected to a voltage source and the patient grounded for monopolar coagulation procedures.

Returning now to FIGS. 8–9, spring 400 biases button 90 outward and spring 402 biases button 100 outward. Catch 300 pivots about pin 406 to engage shelf 404 of button 90 and button 100 drives catch 300 away from engagement with shelf 404 of button 90 when button 100 is pressed in.

Figure 12:
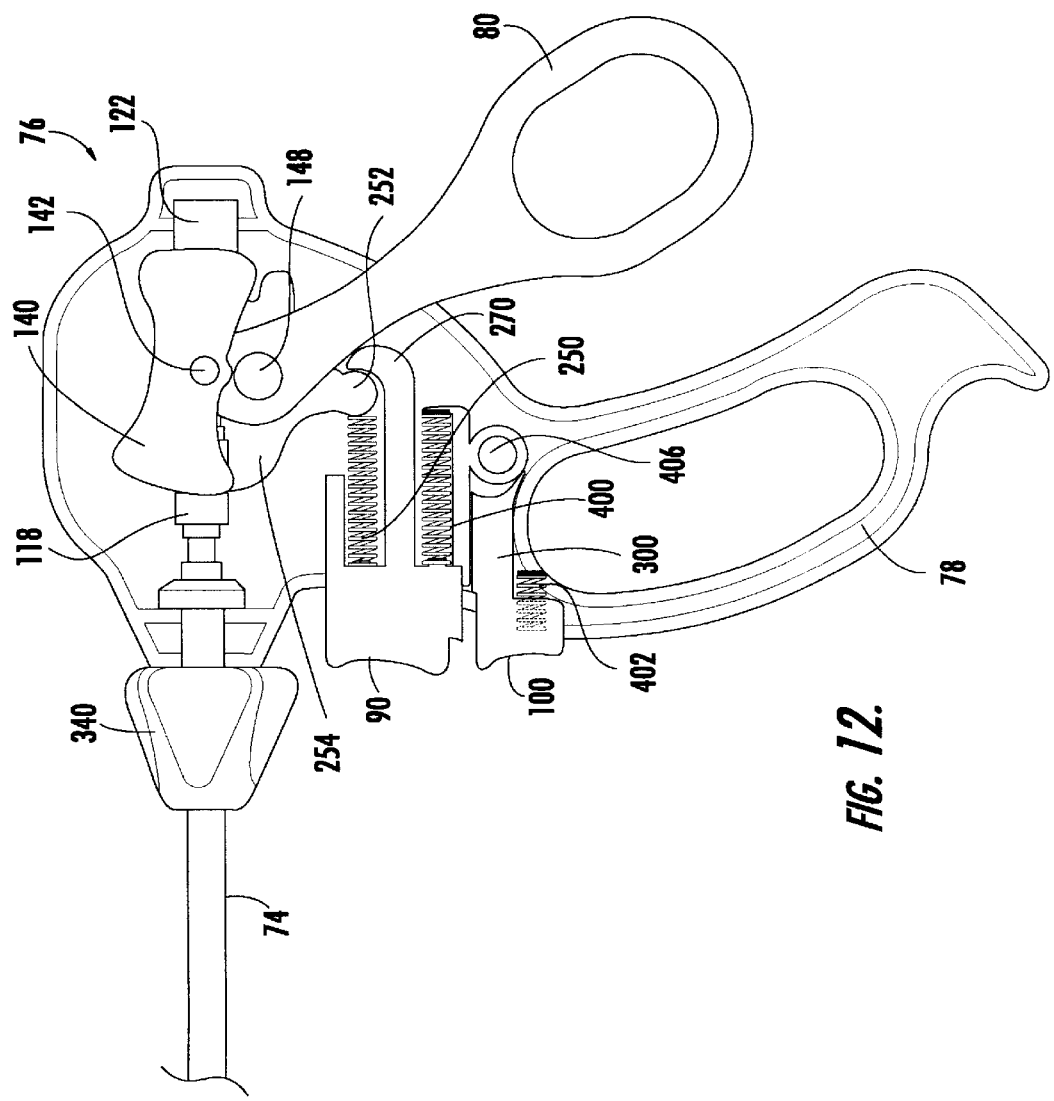
FIG. 12 is another more detailed schematic view of an embodiment of the multi-function surgical instrument handle assembly of the subject invention showing the push button thereof in the release position.
Figure 13:
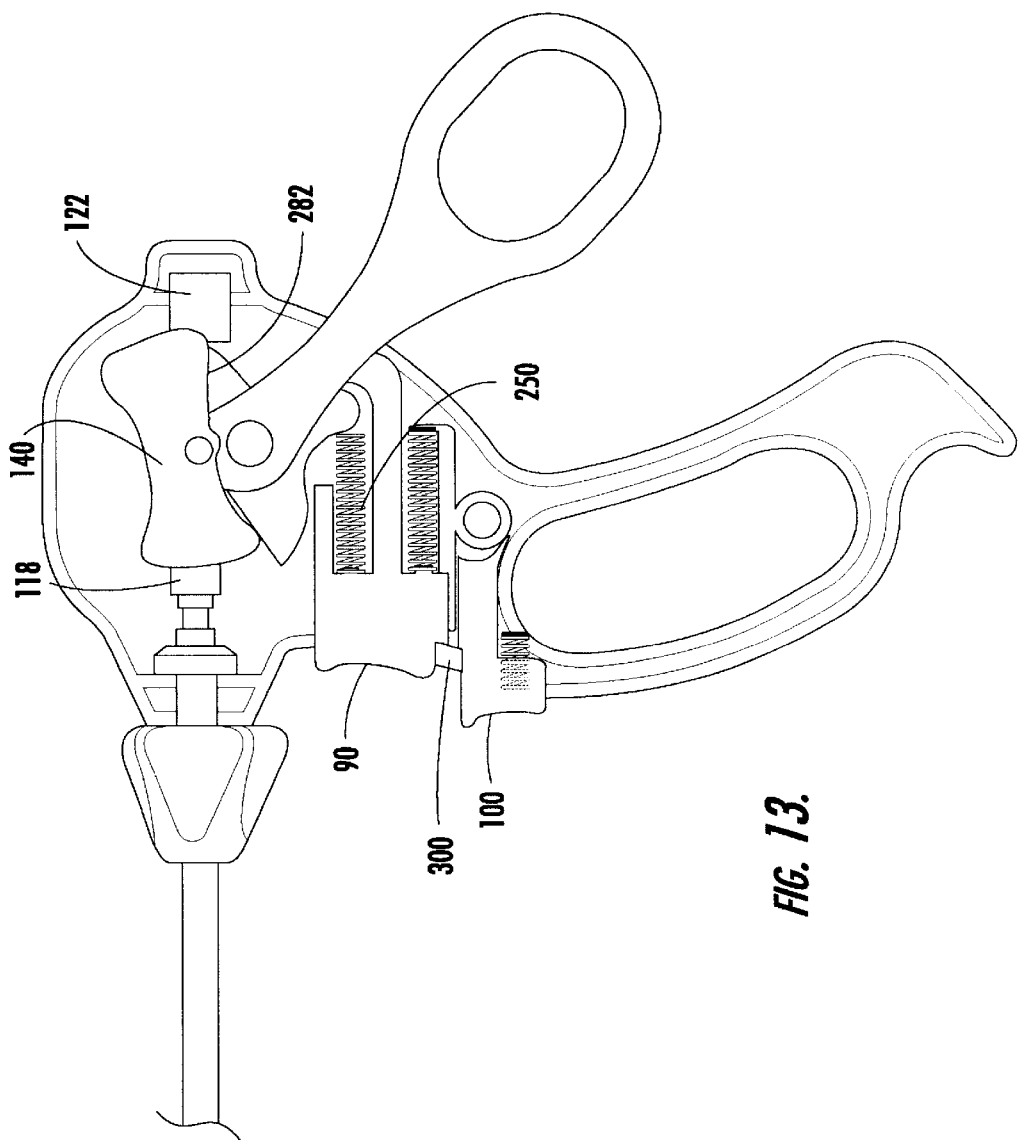
FIG. 13 is a view similar to FIG. 12 except now the push button is depressed.

FIGS. 12–13 show, in part, certain details of the switching mechanism in the prototype device of the subject invention. In FIG. 12, button 90 is released causing drive mechanism 140 to engage rearward coupler 122 while in FIG. 13 button 90 is depressed causing drive mechanism 140 to engage coupler 118. When button 90 is depressed as shown in FIG. 13, spring 250, FIG. 12 will compress but arm 252 of rocking member 254 may not immediately move rearward in FIG. 12 due to the position of coupler 122. But, as the surgeon moves handle 80, coupler 122 which is still engaged by drive mechanism 140 will move into a neutral position as the tissue grasping jaw closes and, in this position, rocking member 254 then pivots about pin 148 under the bias supplied by spring 250. This position is shown in FIG. 13 whereupon drive mechanism 140 now engages coupler 118. The same is true in reverse: when button 90 is released, pawl 270 may not initially move arm 252 of rocking member 254 forward but it is biased to do so via spring 400. As pivoting handle 80 is moved to close the scissor blade, however, the neutral position of coupler 118 is reached whereupon button 90 snaps out and pawl 270 then pulls arm 252 of rocking member 254 completely forward into the position shown in FIG. 12. As stated above, it is preferred that in the closed position, the pressure exerted by pivoting tissue grasping jaw 84, FIG. 4 against fixed member 96 is very low to allow any tissue therebetween to escape when the surgeon moves the laparoscopic instrument. Thus, in FIG. 13, the pressure exerted by spring 250 is designed to allow tissue to escape from between the tissue grasping members and/or the position of stop 282 is adjusted relative to the neutral position of coupler 122 accordingly.

One feature of the subject invention is that the operation of the laparoscopic instrument disclosed herein is fairly self-evident to the surgeon: button 90 is depressed (FIG. 13) to effect cutting operations and button 100 is depressed to effect tissue grasping or coagulation operations (FIG. 12). This two-button operation of the preferred embodiment, however, is not a critical or necessary limitation of the subject invention.

Thus, specific features of the invention are shown in some drawings and not in others. This is for convenience only as each feature may be combined with any or all of the other features in accordance with the invention. And, other embodiments will occur to those skilled in the art and are within the following claims. In particular, the switching mechanism disclosed herein may be useful in devices other than surgical instruments.

What is claimed is:

1. A multi-function surgical instrument comprising:
an end effector assembly including at least first and second movable members;
a first actuator coupled to the first movable member;
a second actuator coupled to the second movable member; and
a handle assembly including:
a drive mechanism, and
a switching mechanism coupled to the drive mechanism and having at least two positions, a first position in which the drive mechanism is engaged with the first actuator to operate the first movable member and, a second position in which the drive mechanism is engaged with the second actuator to operate the second movable member.

2. The surgical instrument of claim 1 in which the handle assembly further includes at least one movable trigger coupled to the drive mechanism.

3. The surgical instrument of claim 1 in which the end effector assembly further includes a stationary member between the first and second movable members.

4. The surgical instrument of claim 3 in which the stationary member has a cutting blade surface and a grasping surface and wherein the first movable member includes a cutting blade surface which cooperates with the cutting blade surface of the stationary member and wherein the second movable member includes a grasping surface which cooperates with the grasping surface of the stationary member.

5. The surgical instrument of claim 1 in which the first and second actuators are lengthy rods extending between the end effector assembly and the handle assembly for laparoscopic procedures.

6. The surgical instrument of claim 5 further including a sheath surrounding the lengthy rods.

7. The surgical instrument of claim 1 further including a first coupler on a proximal end of the first actuator and a second coupler on a proximal end of the second actuator, both couplers configured to be engaged by the drive mechanism.

8. The surgical instrument of claim 7 in which the first and second couplers each include a circumferential groove therein which is engageable by the drive mechanism independent of the orientation of the first and second couplers.

9. The surgical instrument of claim 7 in which the first coupler includes a passageway which slidably receives the second actuator therethrough, the second coupler positioned rearward of the first coupler in the handle assembly.

10. The surgical instrument of claim 9 in which the drive mechanism is pivotably connected to a movable trigger to alternatively engage the first and second couplers.

11. The surgical instrument of claim 10 in which the drive mechanism includes a forward clamp engageable with the first coupler and a rearward clamp engageable with the second coupler.

12. The surgical instrument of claim 11 in which the first coupler includes spaced bushings on opposite sides of the circumferential groove and the forward clamp of the drive mechanism includes an opening which receives the circumferential groove of the first coupler therein when the drive mechanism is pivoted to engage the first coupler.

13. The surgical instrument of claim 11 in which the second coupler includes spaced bushings on opposite sides of the circumferential groove and the rearward clamp of the drive mechanism includes an opening which receives the circumferential groove of the second coupler therein when the drive mechanism is pivoted to engage the second coupler.

14. The surgical instrument of claim 2 in which the handle assembly further includes a stationary trigger spaced from the movable trigger.

15. The surgical instrument of claim 14 in which the stationary trigger is disposed forward of the movable trigger.

16. The surgical instrument of claim 1 in which the switching mechanism includes at least a first button.

17. The surgical instrument of claim 16 in which the switching mechanism further includes a rocking member pivotable between a first position which urges the drive mechanism to engage the first actuator and a second position which urges the drive mechanism to engage the second actuator.

18. The surgical instrument of claim 17 in which the rocking member includes a first locking member which engages the first actuator when the drive mechanism is engaged with the second actuator and a second locking member which engages the second actuator when the drive mechanism is engage with the first actuator.

19. The surgical instrument of claim 17 in which the rocking member includes an arm and the switching mechanism further includes a first spring disposed between the first button and the arm of the rocking member to urge the arm in a first direction when the first button is depressed.

20. The surgical instrument of claim 19 in which the first button includes a pawl oriented to drive the arm of the rocking member in a second direction when the first button moves from a depressed position to an outward position.

21. The surgical instrument of claim 20 in which the switching mechanism further includes a second spring which biases the first button in the outward position to urge the arm of the rocking member in the second direction when the first button is released.

22. The surgical instrument of claim 21 in which the switching mechanism further includes a catch which holds the first button in the depressed position and a second button which, when depressed, releases the catch and the first button.

23. The surgical instrument of claim 22 in which the second button is biased outward.

24. The surgical instrument of claim 1 in which the switching mechanism further includes a lock-out subsystem configured to engage the first actuator when the drive mechanism engages the second actuator and to engage the second actuator when the drive mechanism engages the first actuator.

25. The surgical instrument of claim 1 further including a voltage supply lead electrically connected to one of the first and second movable members for coagulating tissue.

26. The surgical instrument of claim 25 in which there is a voltage supply lead attached to the first actuator and insulation surrounding the first actuator.

27. The surgical instrument of claim 26 in which there is a second voltage supply lead attached to the second actuator.

28. The surgical instrument of claim 1 in which the switching mechanism includes:
a pivotable rocker assembly including a depending arm and forward and rearward shelves which alternately engage the drive mechanism; and
an actuator coupled to the depending arm of the rocker assembly.

29. The surgical instrument of claim 28 in which the actuator is a button including a spring which is disposed to push on the arm of the rocker assembly when the button is depressed, the button further including a pawl biased to pull the arm of the rocker assembly when the button is released.

30. The surgical instrument of claim 28 in which the pivotable rocker assembly further includes forward and rearward stops disposed to engage whichever actuator is not engaged by the drive mechanism.

31. A multi-function laparoscopic instrument comprising:
an end effector assembly including at least first and second movable jaws;
a first actuator coupled to the first movable jaw;
a second actuator coupled to the second movable jaw;
a drive mechanism engageable with the first and second actuators; and
switching means having a first position which orients the drive mechanism to engage the first actuator and a second position which orients the drive mechanism to engage the second actuator for alternatively operating the first and second movable jaws.

32. The laparoscopic instrument of claim 31 in which the first and second movable jaws have a neutral position and the switching means is configured to force the drive mechanism to engage the first or second actuator only when the movable jaws are in the neutral position.

33. The laparoscopic instrument of claim 31 in which the drive mechanism is pivotable forward to engage the first actuator and pivotable rearward to engage the second actuator, and in which the switching means includes a rocker member pivotable in one direction to urge the drive mechanism to pivot forward and pivotable in another direction to urge the drive mechanism to pivot rearward.

34. The laparoscopic instrument of claim 33 in which the rocker member includes an arm and the switching means further includes a first button and a compliant member between the first button and the arm to bias the arm of the rocker in a first direction independent of the position of the drive mechanism when the first button is depressed.

35. The laparoscopic instrument of claim 34 in which the switching means further includes a pawl attached to the first button and a second compliant member disposed to bias the arm of the rocker in a second direction independent of the position of the drive mechanism when the first button is released.

36. A switchable actuator assembly comprising:
a first actuator;
a second actuator;
a forward coupler attached to the proximal end of the first actuator and having a passage which receives the second actuator therethrough;
a rearward coupler on the proximal end of the second actuator;
a pivotable drive mechanism disposed over the forward and rearward couplers; and
a switching mechanism engageable with the pivotable drive mechanism for pivoting the drive mechanism rearward to engage the rearward coupler and forward to engage the forward coupler, the switching mechanism including a rocker member pivotable in a first direction to urge the drive mechanism to pivot rearward and pivotable in a second direction to urge the drive mechanism to pivot forward, the switching mechanism further including an actuator compliantly coupled to the rocking member and operable independent of the position of the first and second actuators.

37. The assembly of claim 36 in which the rocker member includes a forward shelf which urges the drive mechanism to pivot rearward and a rearward shelf which urges the drive mechanism to pivot forward.

38. The assembly of claim 37 in which the rocker member includes a forward locking member which holds the forward coupler stationary when the drive mechanism is engaged with the rearward coupler and a rearward locking member which holds the rearward coupler stationary when the drive mechanism is engaged with the forward coupler.

39. The assembly of claim 38 in which the rocker member includes an arm.

40. The assembly of claim 39 further including a first spring extending between the first actuator and the arm to urge the arm rearward when the actuator is in a first position.

41. The assembly of claim 39 in which the actuator further includes a pawl which urges the arm forward when the actuator is in a second position.

42. The assembly of claim 41 further including a second spring which biases the actuator in the second position.

43. The assembly of claim 40 in which the actuator is a first button and the first position is depressed.

44. The assembly of claim 41 in which the actuator is a first button and the second position is released.

45. The assembly of claim 43 in which the switching mechanism further includes a second button which locks the first button in the depressed position and which is itself depressible to release the first button.

46. A surgical instrument comprising:
an end effector assembly including:
a central fixed jaw with a grasping surface and a cutting surface,
a first movable jaw including a grasping surface which engages the grasping surface of the central fixed jaw to grasp tissue therebetween as the first movable jaw is opened and closed, and
a second movable jaw including a cutting surface which cooperates with the cutting surface of the central fixed jaw to cut tissue therebetween as the second movable jaw is opened and closed;
a first actuator having a proximal end and a distal end coupled to the first movable jaw and which reciprocates to open and close the first movable jaw;
a second actuator having a proximal end and a distal end coupled to the second movable jaw and which reciprocates to open and close the second movable jaw; and
a handle assembly including:
the proximal ends of both the first and second actuators,
a drive mechanism having a first position which engages the proximal end of the first actuator and a second position which engages the proximal end of the second actuator, and
a movable trigger coupled with the drive mechanism to open and close the first movable jaw when the drive mechanism is engaged with the proximal end of the first actuator and to open and close the second movable jaw when the drive mechanism is engaged with the proximal end of the second actuator.

47. The surgical instrument of claim 46 in which the handle assembly further includes a switching mechanism coupled to the drive mechanism to switch it between the first and second positions.

48. A switching system comprising:
a pivotable drive mechanism translatable forward and rearward;
a movable handle pivotable about a first pin and pivotably connected to the drive mechanism by a second pin;
a rocker assembly pivotably disposed about the first pin and including a forward shelf which urges the drive mechanism to pivot in a first direction and a rearward shelf which urges the drive mechanism to pivot in a second direction, the rocker assembly further including an arm depending therefrom; and
an actuator having first and second positions and including a first compliant member which urges the arm of the rocker assembly rearward when the actuator is in the first position to pivot the rocker assembly to engage the rearward shelf thereof with the drive mechanism, the actuator further including a pawl which urges the arm of the rocker assembly forward when the actuator is in the second position to pivot the rocker assembly to engage the forward shelf thereof with the drive mechanism.

49. The switching system of claim 48 in which the actuator is a button depressible to the first position and releasable to the second position.

50. The switching system of claim 48 in which the first compliant member is a spring.

51. The switching system of claim 48 further including a second compliant member which biases the actuator in the second position.

52. The switching system of claim 51 in which the second compliant member is a spring.

53. A multi-function laparoscopic instrument comprising:
an end effector assembly including at least first and second movable members;
a first actuator coupled to the first movable member;
a second actuator coupled to the second movable member; and
a handle assembly including:
a drive mechanism including forward and rearward clamps,
at least one movable trigger pivotably connected with the drive mechanism,
a switch mechanism coupled to the drive mechanism and having at least two positions, a first position in which the drive mechanism is engaged with the first actuator to operate the first movable member when the movable trigger is activated and, a second position in which the drive mechanism is engaged with the second actuator to operate the second movable member when the movable trigger is activated,
a first coupler on a proximal end of the first actuator and a second coupler on a proximal end of the second actuator, each coupler including a circumferential groove therein which is engageable by the drive mechanism independent of the orientation of the first and second couplers, the first coupler including a passageway which slidably receives the second actuator therethrough, the second coupler positioned rearward of the first coupler in the handle assembly, the first coupler including spaced bushings on opposite sides of the circumferential groove therein, the forward clamp of the drive mechanism including an opening which receives the circumferential groove of the first coupler therein when the drive mechanism is pivoted to engage the first coupler, the second coupler including spaced bushings on opposite sides of the circumferential groove therein, the rearward clamp of the drive mechanism including an opening which receives the circumferential groove of the second coupler therein when the drive mechanism is pivoted to engage the second coupler.

54. A multi-function laparoscopic instrument comprising:
an end effector assembly including at least first and second movable members;
a first actuator coupled to the first movable member;
a second actuator coupled to the second movable member; and
a handle assembly including:
a drive mechanism,
at least one movable trigger interconnected with the drive mechanism, and
a switching mechanism coupled to the drive mechanism and having at least two positions, a first position in which the drive mechanism is engaged with the first actuator to operate the first movable member when the movable trigger is activated and, a second position in which the drive mechanism is engaged with the second actuator to operate the second movable member when the movable trigger is activated, the switching mechanism including:
- at least a first button coupled to the drive mechanism, a rocking member pivotable between a first position which urges the drive mechanism to engage the first actuator and a second position which urges the drive mechanism to engage the second actuator, the rocking member including a first locking member which engages the first actuator when the drive mechanism is engaged with the second actuator and a second locking member which engages the second actuator when the drive mechanism is engage with the first actuator.

55. A multi-function laparoscopic instrument comprising:
- an end effector assembly including at least first and second movable members;
- a first actuator coupled to the first movable member;
- a second actuator coupled to the second movable member; and
- a handle assembly including:
  - a drive mechanism,
  - at least one movable trigger interconnected with the drive mechanism, and
  - a switching mechanism coupled to the drive mechanism and having at least two positions, a first position in which the drive mechanism is engaged with the first actuator to operate the first movable member when the movable trigger is activated and, a second position in which the drive mechanism is engaged with the second actuator to operate the second movable member when the movable trigger is activated, the switching mechanism including:
    - at least a first button including a pawl, a rocking member including an arm and pivotable between a first position which urges the drive mechanism to engage the first actuator and a second position which urges the drive mechanism to engage the second actuator, the rocking member further including a first locking member which engages the first actuator when the drive mechanism engages the second actuator and a second locking mechanism which engages the second actuator when the drive mechanism is engaged with the first actuator,
    - a first spring disposed between the first button and the arm of the rocking member which urges the arm rearward when the first button is depressed,
    - a second spring which biases the first button in the outward position to urge the pawl of the first button to move the arm of the rocking member forward when the first button is released,
    - a catch which holds the first button in the depressed position, and
    - a second button which, when depressed, releases the catch and the first button.

* * * * *